US011485985B2

(12) United States Patent
Goeke et al.

(10) Patent No.: US 11,485,985 B2
(45) Date of Patent: Nov. 1, 2022

(54) PRODUCTION OF GUAIENE AND ROTUNDONE

(71) Applicant: Givaudan SA, Vernier (CH)

(72) Inventors: Andreas Goeke, Dübendorf (CH); Julie Charpentier, Zürich (CH); Boris Schilling, Knonau (CH); Fridtjof Schröder, Hettlingen (CH)

(73) Assignee: Givaudan SA, Vernier (CH)

( * ) Notice: Subject to any disclaimer, the term of this patent is extended or adjusted under 35 U.S.C. 154(b) by 73 days.

(21) Appl. No.: 16/765,649

(22) PCT Filed: Nov. 21, 2018

(86) PCT No.: PCT/EP2018/082007
§ 371 (c)(1),
(2) Date: May 20, 2020

(87) PCT Pub. No.: WO2019/110299
PCT Pub. Date: Jun. 13, 2019

(65) Prior Publication Data
US 2020/0299737 A1    Sep. 24, 2020

(30) Foreign Application Priority Data

Dec. 5, 2017   (EP) .................................... 17205361

(51) Int. Cl.
| | |
|---|---|
| *C12P 7/38* | (2006.01) |
| *A23L 27/20* | (2016.01) |
| *A23L 27/10* | (2016.01) |
| *C07C 45/27* | (2006.01) |
| *C12N 9/88* | (2006.01) |

(52) U.S. Cl.
CPC ................. *C12P 7/38* (2013.01); *A23L 27/10* (2016.08); *A23L 27/203* (2016.08); *C07C 45/27* (2013.01); *C12N 9/88* (2013.01); *A23V 2002/00* (2013.01)

(58) Field of Classification Search
None
See application file for complete search history.

(56) References Cited

U.S. PATENT DOCUMENTS 10,392,673 B2 *   8/2019   Kino ............... C12Y 111/02004
2013/0172625 A1 *  7/2013   Tarbit ....................... B01J 21/18
568/360

FOREIGN PATENT DOCUMENTS

| EP | 3255151 A2 | 12/2017 |
|---|---|---|
| WO | 2005052163 A2 | 6/2005 |

OTHER PUBLICATIONS

Yesilirmak and Sayers, "Heterologous Expression of Plant Genes", International Journal of Plant Genomics, Article ID 296482, pp. 1-16. (Year: 2009).*
Fabienne Deguerry, et al., The diverse sesquiterpene profile of patchouli, Pogostemon cablin, is correlated with a limited number of sesquiterpene synthases, Archives of Biochemistry and Biophysics, Aug. 23, 2006, pp. 123-126, vol. 454, Elsevier Inc.
Arctander, 1994, vol. I.
Tatiana A. Tatusova, et al., BLAST 2 Sequences, a new tool for comparing protein and nucleotide sequences, FEMS Microbiology Letters, Mar. 18, 1999, pp. 247-250, vol. 174, Elsevier Science B V.
Firmenich SA, Clearwood Technical disclosure, by Firmenich SA, IP.com No. IPCOM000233341D, Dec. 9, 2013.
Claudia Wood, et al., From Wine to Pepper: Rotundone, an Obscure Sesquiterpene, Is a Potent Spicy Aroma Compound, Journal of Agricultural and Food Chemistry, 2008, pp. 3738-3744, vol. 56, Issue 10, American Chemical Society.
An-Cheng Huang, et al., Production of the Pepper Aroma Compound, (−)-Rotundone, by Aerial Oxidation of a-Guaiene, Journal of Agricultural and Food Chemistry, Oct. 11, 2014, pp. 10809-10815, vol. 62, ACS Publications.
Akira Nakanishi, et al., Identification of Rotundone as a Potent Odor-Active Compound of Several Kinds of Fruits, Journal of Agricultural and Food Chemistry, May 18, 2017, pp. 4464-4471, vol. 65, ACS Publications.
Hideki Takase, et al., Cytochrome P450 CYP71BE5 in grapewine (*Vitis vinifera*) catalyzes the formation of the spicy aroma compound (−)-rotundone, Journal of Experimental Botany, 2016, pp. 787-798, vol. 67, Oxford University Press.
An-Cheng Huang, et al., Mechanistic Studies on the Autoxidation of a-Guaiene: Structural Diversity of the Sesquiterpenoid Downstream Products, Journal of Natural Products, Jan. 12, 2015, pp. 131-145, vol. 78, ACS Publications.
Evan J. Horn, et al., Scalable and sustainable electrochemical allylic C—H oxidation, Nature, May 5, 2016, pp. 77-81, vol. 533, MacMillan Publishers Limited.
Drew, Damian Paul. "Two key polymorphisms in a newly discovered allele of the Vitis vinifera TPS24 gene are responsible for the production of the rotundone precursor α-guaiene." Journal of Experimental Botany, vol. 67, No. 3 pp. 799-808, Nov. 17, 2015.
XP002783297, Database EMBL [Online], Database Accession No. GU083698, "Aquilaria crassna delta-guaiene synthase c(3) mRNA, complete cds." Nov. 4, 2009.

(Continued)

*Primary Examiner* — Anand U Desai
(74) *Attorney, Agent, or Firm* — Curatolo, Sidoti & Trillis Co., LPA; Salvatore A. Sidoti; Brittany L. Kulwicki

(57) ABSTRACT

A process for producing rotundone from α-guaiene, in particular by oxidation of the C(3) position, wherein the α-guaiene is produced from a precursor by a sesquiterpene synthase. The sesquiterpene synthase is produced in a microorganism.

15 Claims, No Drawings
Specification includes a Sequence Listing.

(56) References Cited

OTHER PUBLICATIONS

XP055494816, Kumeta et al. "Characterization of delta-guaiene Synthases from Cultured Cells of Aquilaria, Responsible for the Formation of Sesquiterpenes in Agarwood." Plant Physiology, vol. 154, No. 4, pp. 1998-2007, Oct. 2010.
Mattivi, Fulvio. "Key enzymes behind black pepper aroma in wines." Journal of Experimental Botany, vol. 67, No. 3, pp. 555-557, Feb. 2, 2016.
PCT International Search Report for PCT/EP2018/082007, dated Mar. 28, 2019.
PCT Written Opinion for PCT/EP2018/082007, dated Mar. 28, 2019.
European Patent Office, Extended Search Report for EP 17205361.3, dated Aug. 6, 2018.

* cited by examiner

PRODUCTION OF GUAIENE AND ROTUNDONE

CROSS REFERENCE TO RELATED APPLICATIONS

This application is a national stage application of International Application No. PCT/EP2018/082007, filed 21 Nov. 2018, which claims priority from European Patent Application No. 17205361.3, filed 5 Dec. 2017, both of which applications are incorporated herein by reference in their entireties.

SEQUENCE LISTING

Attached to this Amendment is a Sequence Listing as filed in the PCT International Application. The Sequence Listing includes sequences for SEQ ID NOs. 1-6. Please amend the present application to include the Sequence Listing.

The present invention relates to a process for producing rotundone from α-guaiene, to a use of α-guaiene for producing rotundone, to fragrance or flavor ingredients and to a use of such fragrance or flavor ingredients.

Rotundone ((3S,5R,8S)-3,8-dimethyl-5-prop-1-en-2-yl-3,4,5,6,7,8-hexahydro-2H-azulen-1-one) is a sesquiterpene originally discovered in the tubers of *Cyperus rotundus*. The compound has a strong spicy peppercorn aroma and a woody odor. It was later also found to be a constituent of black and white pepper, marjoram, oregano, rosemary, basil, thyme, geranium, agarwood, patchouli oil and cypriol oil.

Furthermore, rotundone was detected in various wines that exhibit peppery spicy notes, mainly Syrah (Shiraz) wines. The sesquiterpene has an aroma detection threshold in water of 8 ng/L, which is amongst the lowest for any natural product yet discovered (*J. Agric. Food Chem.* 2008, 56, 3738-3744 and references cited therein).

Moreover, an investigation of the aromas of grapefruit, orange, apple, and mango revealed the presence of rotundone. Sensory analyses showed that the compound, when added at even subthreshold levels to model beverages of these fruits, did not confer directly a woody odor, but had significant effects on the overall flavors of the beverages, helping them to better approximate the natural flavors of the fruits (*J. Agric. Food Chem.* 2017, 65, 4464-4471).

Despite these highly attractive properties, rotundone has not been used as an ingredient in the fragrance and flavor industry thus far. A main reason for this is the fact that there is no reliable process for the production of sufficient amounts of this material in the desired olfactive quality.

It is surmised that in nature rotundone is formed from α-guaiene by allylic oxidation of the C(3) position, either by aerial oxidation, reactive oxygen species (ROS) or enzymatic oxidation (*J. Agric. Food Chem.* 2014, 62, 10809-10815; *J. Nat. Prod.* 2015, 78, 131-145; *J. Exp. Bot.* 2016, 67, 787-798). This transformation can also be achieved by means of chemical synthesis.

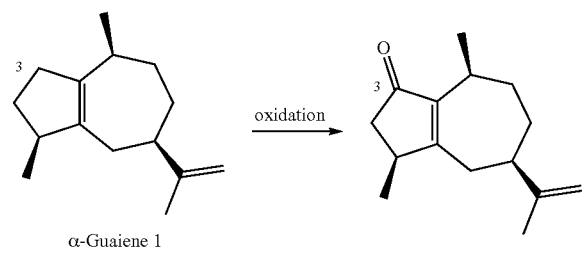

α-Guaiene 1 → oxidation → Rotundone 2

α-Guaiene is a constituent of various essential oils, such as guaiacwood oil or patchouli oil. Although it is widely employed in the field of fragrances and flavors, it hitherto could not be used as a precursor for the industrial production of rotundone. First of all, there are serious limitations in the supply of plant materials, from which α-guaiene can be extracted, as many of these are harvested from endangered species, the exploitation of which is under strict control. Furthermore, the separation of α-guaiene from plant extracts is difficult and a major hurdle to access this precursor. Also, the quality of such extracts often suffers from considerable fluctuations. For example, the odor of guaiacwood has been reported to be accompanied by a "smoked ham"-like odor, conceivably acquired during forced distillation of the guaiacwood in adding mineral acid to the distillation water in order to increase the yield and speed of the distillation (S. Arctander, *Perfume and Flavor Materials of Natural Origin* 1994, Allured Publishing Corporation, Carol Stream, Ill., USA). The impurities causing this "smoked ham"-like odor are difficult to separate, either from α-guaiene or from rotundone after conversion.

It is therefore a problem underlying the present invention to overcome the above-mentioned shortcomings in the prior art. In particular, it is a problem underlying the present invention to provide a process for the production of rotundone for use in the fragrance and flavor industry, more specifically in the substantial absence of impurities causing a disturbing odor, in particular of the above mentioned "smoked ham"-like odor. Advantageously, this process is supposed to allow for the production of significant quantities of rotundone. Furthermore, the process should be environmentally friendly, safe and cost-efficient.

These problems are solved by a process according to claim 1. In this process, rotundone is produced from α-guaiene, in particular by oxidation of the C(3) position. The α-guaiene is produced from a precursor by a sesquiterpene synthase, wherein the sesquiterpene synthase is produced in a microorganism.

In the context of the present invention, the term "sesquiterpene synthase" refers to a polypeptide capable of effecting the synthesis of the sesquiterpene α-guaiene from a precursor.

Furthermore, that "the α-guaiene is produced from a precursor by a sesquiterpene synthase" is to be understood that the precursor and the sesquiterpene synthase are brought in contact with each other in order to effect the formation of α-guaiene.

Another aspect of the present invention refers to a process for producing rotundone comprising the steps of:
Producing a sesquiterpene synthase in a microorganism;
Producing α-guaiene by bringing the sesquiterpene synthase obtained into contact with a precursor;
Producing rotundone from the α-guaiene obtained, in particular by oxidation of the C(3) position.

By use of a sesquiterpene synthase that is produced in a microorganism, α-guaiene can be obtained independently from naturally sourced raw materials, more specifically through a biotechnological process. Without this constraint, significant quantities of rotundone can be produced at industrial scale with no limitations in volumes, using an environmentally friendly process. This allows for the sustainable production of this compound, in particular as an ingredient in the fragrance and flavor industry. Furthermore, due to the fact that no extraction of plant material is necessary, the α-guaiene required can be furnished under controlled conditions in stable quality and in the substantial absence of impurities causing a disturbing odor, in particular of the above mentioned "smoked ham"-like odor.

The microorganism can be cultured under conditions suitable to produce α-guaiene, in particular in vivo. This has the advantage that the production of both of the sesquiterpene synthase and the α-guaiene can be effected in the same biotransformation, which makes the overall process more efficient. Furthermore, isolation of the sesquiterpene synthase is avoided.

In a preferred embodiment, the microorganism is cultured under conditions suitable to also produce the precursor, in particular from a sugar. Examples of suitable sugars include, but are not limited to, sucrose, fructose, xylose, glycerol, glucose, cellulose, starch, cellobiose and other glucose containing polymers.

On the other hand, the sesquiterpene synthase can also be isolated from the microorganism prior to the production of α-guaiene. Although an additional transformation is then required, the formation of the α-guaiene can then be effected ex vivo under more controlled conditions.

The sesquiterpene synthase required to effect the formation of α-guaiene ex vivo can be obtained by extraction from any microorganism expressing it, using standard protein or enzyme extraction technologies.

If the microorganism is a cell releasing the sesquiterpene synthase into the culture medium, the sesquiterpene synthase may simply be collected from the culture medium, for example by centrifugation, optionally followed by washing steps and re-suspension in suitable buffer solutions. If the microorganism accumulates the polypeptide within itself, the sesquiterpene synthase may be obtained by disruption or lysis of the cells and further extraction of the polypeptide from the cell lysate.

The sesquiterpene synthase, either in isolated form or together with other proteins, for example in a crude protein extract obtained from the cultured microorganism, may then be suspended in a buffer solution at optimal pH. If adequate, salts, BSA and other kinds of enzymatic co-factors, may be added in order to optimize enzyme activity. In particular, the enzymatic co-factor can be a $Mg^{2+}$ salt.

The precursor may then be added to the suspension or solution, which is then incubated at optimal temperature, for example between 15 and 40° C., preferably between 25 and 35° C., more preferably at 30° C. After incubation, the α-guaiene, and optionally the other sesquiterpene by-products may be isolated from the incubated solution by standard isolation procedures, such as solvent extraction and distillation, optionally after removal of polypeptides from the solution.

The microorganism can be a recombinant microorganism. The term "recombinant microorganism" refers to a microorganism that is transformed to express the sesquiterpene synthase, preferably under conditions conductive to the production of α-guaiene. The term "transformed" refers to the fact that the microorganism was subjected to genetic engineering. Preferably, the microorganism is heterologously expressing the sesquiterpene synthase or even overexpressing it. There are several methods known in the art for the creation of transgenic microorganisms.

The recombinant microorganism can be a bacterium or a yeast. More specifically, the microorganism can be selected from the group consisting of *Escherichia coli, Arxula adeninivorans, Candida boidinii, Hansenula polymorpha, Kluyveromyces lactis, Pichia pastoris, Saccharomyces cerevisiae* and *Yarrowia lipolytica*.

Preferably, the *Escherichia coli* used is recognized by the industry and regulatory authorities (including but not limited to an *Escherichia coli* K12 or an *Escherichia coli* BL21).

The precursor can be an acyclic precursor, in particular farnesyl pyrophosphate. In a preferred embodiment of the present invention, wherein the α-guaiene is formed in vivo, the microorganism is also capable of producing farnesyl pyrophosphate, preferably from a sugar.

The sesquiterpene synthase can have a sequence identity with SEQ ID NO.: 2, SEQ ID NO.: 4 or SEQ ID No.: 6 of at least 70%, preferably at least 80%, more preferably at least 90%, even more preferably at least 95%.

SEQ ID NO.: 2 corresponds to the enzyme VvGuaS, which was obtained from *Vitis vinifera*, as described in *J. Exp. Bot.* 2016, 67, 799-808. SEQ ID NO.: 1 represents the corresponding nucleic acid sequence. VvGuaS has been shown to produce α-guaiene as a main product with 45% selectivity.

SEQ ID NO.:4 corresponds to the enzyme AcC3, which was obtained from *Aquilaria* plants, as described in *Plant Physiol.* 2010, 154, 1998-2007. SEQ ID NO.: 3 represents the corresponding nucleic acid sequence. AcC3 has been shown to produce α-guaiene with 45% selectivity.

SEQ ID NO.: 6 corresponds to the enzyme PatTps717, which was obtained from *Pogostemon cablin* (patchouli), as described in *Arch. Biochem. Biophys.* 2006, 454, 123-136. SEQ ID NO.: 5 represents the corresponding nucleic acid sequence (cf. also NCBI GenBank accession number AY508730 {Version: AY508730.1}). PatTps717 has been shown to produce α-guaiene with 13% selectivity.

The sequence identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs. Preferably, the BLAST program (*FEMS Microbiol Lett.* 1999, 174, 247-250) set to the default parameters, available from the National Center for Biotechnology Information (NCBI) can be used to obtain an optimal alignment of peptidic or nucleotidic sequences and to calculate the percentage of sequence identity.

In the context of the present invention, another microorganism can be transformed capable of producing the sesquiterpene synthase with at least one nucleic acid encoding the sesquiterpene synthase.

The at least one nucleic acid can have a sequence identity with SEQ ID NO.: 1, SEQ ID NO.: 3 or SEQ ID No.: 5 of at least 70%, preferably at least 80%, more preferably at least 90%, even more preferably at least 95%.

The "nucleic acid" can be defined as including deoxyribonucleotide or ribonucleotide polymers in either single- or double-stranded form (DNA and/or RNA). An important tool for transforming microorganisms cells suitable to produce the sesquiterpene synthase is an expression vector comprising a nucleic acid. An "expression vector" as used herein includes any linear or circular recombinant vector including but not limited to plasmids, phagemids, phages, cosmids, artificial bacterial or artificial yeast chromosomes, and knock-out or knock-in constructs. The skilled person is capable of selecting a suitable vector according to the expression system.

A bacterial or yeast cell may be transformed by exogenous or heterologous DNA when such DNA has been introduced inside the cell. The transforming DNA may or may not be integrated, i.e. covalently linked into the genome of the cell. In prokaryotes, and yeast, for example, the transforming DNA may be maintained on an episomal element such as a plasmid. With respect to eukaryotic cells, a stably transfected cell is one in which the transfected DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

In the context of the present invention, bacteria (for example *Escherichia coli*) can be transformed with, for example, recombinant bacteriophage DNA, plasmid DNA, bacterial artificial chromosome, or cosmid DNA expression vectors. Yeasts (for example *Saccharomyces cerevisiae*) can be transformed with, for example, recombinant yeast expression vectors containing the polynucleotide molecule of the disclosure. Depending on the microorganism and the respective vector used, the polynucleotide can integrate, for example, into the chromosome or the mitochondrial DNA or can be maintained extrachromosomally like, for example, episomally or can be only transiently comprised.

The suitability of a microorganism for use according to the present invention may be determined by simple test procedures using well known methods. For example, the microorganism to be tested may be propagated in a rich medium (e.g. LB-medium, Bactotryptone yeast extract medium or nutrient medium) at a pH, temperature and under aeration conditions commonly used for propagation of the microorganism. Once a microorganisms is selected that produces the desired products of bioconversion, the products are typically produced by a production cell line on the large scale by suitable expression and fermentations, i.e. by microbial production in cell culture.

For cell cultivation, a defined minimal medium such as M9A can be used. The components of M9A medium comprise: 14 g/L $KH_2PO_4$, 16 g/L $K_2HPO_4$, 1 g/L $Na_3Citrate.2H_2O$, 7.5 g/L $(NH_4)_2SO_4$, 0.25 g/L $MgSO_4.7H_2O$, 0.015 g/L $CaCl_2.2H_2O$, 5 g/L glucose and 1.25 g/L yeast extract. On the other hand, a nutrient rich medium such as LB can be used. The components of LB medium comprise: 10 g/L tryptone, 5 g/L yeast extract and 5 g/L NaCl.

The microorganism may be grown in a batch, fed batch or continuous process or combinations thereof. Typically, the microorganism is grown in a fermenter at a defined temperature(s) in the presence of a suitable nutrient source for a desired period of. As used herein, the term "batch cultivation" is a cultivation method in which culture medium is neither added nor withdrawn during the cultivation. As used herein, the term "fed-batch" means a cultivation method in which culture medium is added during the cultivation but no culture medium is withdrawn.

The process according to the present invention can further comprise the step of purifying the α-guaiene prior to the production of rotundone, in particular by distillation or chromatography. Advantageously, the α-guaiene used for producing rotundone has a purity of 10 to 95%, preferably 20 to 80%, more preferably 30 to 70%.

In a process according to the present invention, rotundone can be produced from α-guaiene by an oxidation selected from the group consisting of transition metal catalysis, organocatalysis, chromium oxidation, selenium oxidation, manganese oxidation, aerial oxidation, enzymatic oxidation, electrochemical oxidation and combinations thereof. This bestows significant flexibility with regard to the means available to effect this transformation.

In order to avoid any ambiguity, in the context of the present invention, "oxidation of α-guaiene at the C(3) position", is not only to be understood as a direct oxidation of the methylene group at the C(3) position of α-guaiene to the corresponding carbonyl group. This transformation can also refer to a process, wherein the carbonyl group is formed stepwise via an intermediate, for instance a secondary alcohol. Depending on the method used, this intermediate can be isolated and further transformed into rotundone.

In the context of the present invention "aerial oxidation" is to be understood as any oxidation with molecular oxygen ($O_2$), either in pure or dilute form, for instance as air.

When rotundone is produced from α-guaiene by transition metal catalysis, the transition metal can be selected from the group costing of iron, copper, vanadium, manganese, molybdenum, cobalt, ruthenium, palladium, iridium, rhodium, titanium, chromium, gold, osmium and combinations thereof. With these transition metals, high selectivities for the product rotundone and good yields can be achieved.

In particular, rotundone can be produced from α-guaiene by iron porphyrin catalysis comprising the steps of:
Forming a mixture containing α-guaiene and an iron (III)-X porphyrin complex catalyst in a solvent;
Introducing molecular oxygen into the mixture;
Effecting production of rotundone by oxidation of the C(3) position of α-guaiene.

Iron porphyrin catalysis provides an efficient method for the transformation of α-guaiene to rotundone with good selectivies and yields. Molecular oxygen ($O_2$) is a superb stoichiometric oxidant that is readily available, cost-efficient, environmentally friendly and save to handle. Also the iron (III)-X porphyrin complex catalysts show a low toxicity and can be used with a low catalyst loading. Furthermore, the odor profiles of the crude products are such, that the odor of rotundone is not adversely affected by byproducts. As a consequence of this, depending on the application, the products obtained can be used in the perfume and flavor industry without purification of rotundone. If however, the rotundone obtained is to be purified, this can be achieved through a simple distillation or by column chromatography.

In the above-described iron porphyrin catalysis, X can be selected from Cl, Br, I, mesylate, triflate and carboxylates, preferably Cl, Br and I. Especially Cl is preferred, as with this anion, a variety of iron (III)-X porphyrin complex catalysts can be obtained at low costs from commercial sources with different substitution patterns at the porphyrin system.

In the above-described iron porphyrin catalysis, the mixture can additionally contain a base coordination compound, preferably an N-heterocycle, more preferably imidazole. This has the advantage that better yields and purities are achieved after short reaction times.

On one hand, the step of introducing molecular oxygen into the mixture can comprise bubbling oxygen gas into the mixture. On the other hand, the step of introducing molecular oxygen into the mixture can also comprise bubbling air into the mixture.

Another option for introducing molecular oxygen into the mixture is to heavily stir the mixture under an oxygen containing atmosphere. It has been found that good results can be achieved in the above-described iron porphyrin catalysis by the introduction of either air or molecular oxygen into the reaction mixture. Air as the source of molecular oxygen has the further advantage that it is abundantly available at low cost. Furthermore it is operationally safe.

Although not required, the process may include exposing the mixture to electromagnetic radiation, preferably UV light radiation or radiation in the visible range of the electromagnetic spectrum. The wavelength range of electromagnetic radiation used to expose the mixture may be in the range of about 200 nm to about 800 nm. Alternatively, the process may be carried out in the dark or under ambient light conditions. The possibility to choose among these options allows the choice of the most suitable setup for industrial production.

In the iron porphyrin catalysis, the solvent can be selected from the group consisting of water, acetone, ethanol, 2-propanol, ethyl acetate, isopropyl acetate, methanol, methyl ethyl ketone, 1-butanol, tert-butanol and mixtures thereof, preferably an ethanol/water mixture. These solvents can be either discarded without environmental damage or easily recycled after use. An ethanol/water mixture has the further advantage that rotundone can be obtained in particular good yield and purity. Furthermore, with an ethanol:water ratio of less than 1:1, a non-flammable mixture can be achieved.

On the other hand, the solvent can also be selected from the group consisting of cyclohexane, heptane, toluene, methylcyclohexane, methyl tert-butyl ether, isooctane, acetonitrile, xylenes, dimethyl sulfoxide, acetic acid, ethylene glycol and mixtures thereof.

Preferably, the catalyst is an iron (III) porphyrin complex catalyst, having a chloride counter-ion. Furthermore, the porphyrin complex can be a tetraphenylporphyrin complex. Specifically, the catalyst can be chloro(tetraphenylporphyrinato)iron(III). Using this catalyst, superb results with respect to selectivity, yield and product purity can be achieved. Furthermore, as mentioned above, this catalyst is cost-effective and available from commercial sources. However, catalysts of this type with different substitution patterns at the porphyrin can be easily and nearly quantitatively prepared from even less expensive components $Fe(II)Cl_2$ and the porphyrine ligand. In addition, chloro(tetraphenylporphyrinato)iron-(III) can be employed with low catalyst loadings. Furthermore, hemine chloride can be used as an iron (III)-X porphyrin complex catalyst.

Alternatively, rotundone can be produced from α-guaiene by cobalt catalysis, in particular comprising the steps of:
Forming a mixture containing α-guaiene and at least one cobalt (II) complex catalyst, preferably selected from the group consisting of cobalt(II) ethylhexanoate, cobalt(II) acetylacetonate, cobalt(II) naphthenate and mixtures thereof, in particular in the presence of 4-methyl-2-pentanone, in a solvent;
Introducing molecular oxygen into the mixture;
Effecting oxidation of the C(3) position of α-guaiene.

As yet another alternative, rotundone can be produced from α-guaiene by chromium oxidation, in particular comprising the steps of:

Forming a mixture containing α-guaiene and at least one chromium reagent, preferably a chromium (VI) reagent, in particular selected from the group consisting of pyridinium chlorochromate, pyridinium fluorochromate, pyridinium dichromate, chromium trioxide, sodium chromate and mixtures thereof, preferably in the presence of celite, in a solvent;
Effecting oxidation of the C(3) position of α-guaiene.

With this method, rotundone can be obtained in good yield and purity.

Moreover, rotundone can be produced from α-guaiene by organocatalysis, in particular comprising the steps of:
Forming a mixture containing α-guaiene, an organocatalyst, preferably selected from the group consisting of N-hydroxyphthalimide and tetrachloro-N-hydroxyphthalimide, and an oxidant in a solvent;
Effecting oxidation of the C(3) position of α-guaiene.

Through organocatalysis, production of rotundone from α-guaiene can be achieved without the use of expensive and potentially harmful heavy metal catalysts. This process is therefore cost-efficient, environmentally friendly and operationally safe.

In the organocatalysis, the oxidant can be selected from the group consisting of tert-butyl hydroperoxide, hydrogen peroxide, dibenzoyl peroxide, di-tert-butyl peroxide, sodium chlorite, molecular oxygen and mixtures thereof. All of these oxidants are bulk chemicals that are readily available and safe in use. Sodium chlorite and molecular oxygen have the further advantage that work-up of the reaction is particularly facile.

In the context of the present invention, rotundone can also be produced from α-guaiene by electrochemical oxidation, in particular comprising the steps of:
Forming a mixture containing α-guaiene, an electrochemical mediator, preferably selected from the group consisting of N-hydroxyphthalimide and tetrachloro-N-hydroxyphthalimide, and an electrolyte in a solvent;
Applying an electrical current to the mixture;
Effecting oxidation of the C(3) position of α-guaiene.

A representative example of electrochemical oxidation is described in *Nature* 2016, 533, 77-81. It allows for the production of rotundone from α-guaiene in good yield and selectivity. By electrochemical oxidation, no or less stoichiometric oxidants need to be used and the generation of waste products is reduced.

In the above-described electrochemical oxidation, the mixture can additionally contain a base, preferably selected from the group consisting of pyridine, 2,6-lutidinie, 2,4,6-collidine, trimethylamine, DBU and mixtures thereof. The solvent can be selected from the group consisting of acetone, acetonitrile, dichloromethane, pyridine and mixtures thereof. The electrolyte can be selected from the group consisting of $LiBF_4$, $LiClO_4$ and mixtures thereof.

Furthermore, in the above-described electrochemical oxidation, the mixture additionally contains a co-oxidant, preferably selected from the group consisting of tert-butyl hydroperoxide, hydrogen peroxide, dibenzoyl peroxide, di-tert-butyl peroxide and mixtures thereof. By use of a co-oxidant increased yields can be achieved.

Apart from chemical synthesis, rotundone can also be produced from α-guaiene by enzymatic oxidation, in particular through an enzyme selected from the group consisting of a cytochrome P450, preferably an α-guaiene 3-oxidase cytochrome P450, a laccase, a Rieske non-heme dioxygenase and combinations thereof. An α-guaiene 3-oxidase cytochrome P450 (referred therein as "α-guaiene 2-oxidase VvSTO2") has been described in *J. Exp. Bot.*

2016, 67, 787-798. This enzyme has been shown to exhibit excellent substrate-specificity and selectivity.

An oxidation of α-guaiene at the C(3) position with the above-mentioned enzymes can also lead to a corresponding secondary alcohol. This intermediate can be further oxidized to rotundone using various methods, for instance oxidation with an alcohol oxidase or an alcohol dehydrogenase.

A process according to the present invention can further comprise the step of purifying the rotundone produced. This can be effected by distillation or chromatography. Distillation has the advantage that it can be performed at low cost on large scales. The advantage of chromatography is that material with a particularly high purity can be obtained.

The present invention also refers to a use of α-guaiene for producing rotundone, in particular by oxidation of the C(3) position, wherein the α-guaiene is produced from a precursor, in particular an acyclic precursor, by a sesquiterpene synthase, wherein the sesquiterpene synthase is produced in a microorganism.

A further aspect of the present invention relates to a fragrance or flavor ingredient obtainable by the process as stated hereinabove.

The present invention also refers to a fragrance or flavor ingredient, in particular an ingredient as described hereinabove, wherein the portion of rotundone is in a range of 10 to 95 wt.-%, preferably 20 to 70 wt.-%, even more preferably 25 to 50 wt.-%.

The fragrance or flavor ingredient can additionally contain ketone 5.

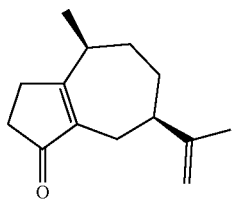

5

In such a fragrance or flavor ingredient, the weight-ratio of rotundone to ketone 5 can be in a range of 20:1 to 1:1, preferably 10:1 to 2:1, even more preferably 5:1 to 3:1.

The present invention also relates to a consumer product containing a fragrance or flavor ingredient as stated herein above and to the use of such a fragrance or flavor ingredient.

The present invention also refers to a process for producing a fragrance or flavor composition and/or a consumer product, the process comprising the production of rotundone from α-guaiene by a process as described herein above.

Further aspects and particular features of the present invention become apparent from the following description of representative embodiments.

Analytical Methods Employed
Polar GCMS:
35° C./2 min, 10° C./min to 50° C., 2.5° C./min to 240° C., 240° C./5 min. Thermo Scientific TSQ8000evo+Trace 1310 system. Polar column: Varian VF-WAX (polar, PEG phase). Column dimensions: 30 m length, 0.25 mm ID, 0.25 μm film thickness. Injector: splitless. Flow: 1.2 mL/min. Carrier gas: Helium. Injection volume: 1 μl. Injector temperature: 230° C. Transfer line: 250° C. MS-quadrupol: 160° C. MS-source: 230° C. Ionization mode: Electron Impact (EI) at 70 eV.

By this method, the products obtained were identified. Minor and unidentified byproducts were neglected and their percentages (usually <10%) are not given. Apart from α-guaiene 1 and rotundone 2, side products included rotundol 3, epoxy-guaiene 4, ketone 5, hydroxy-rotundone 6, and corymbolon 7.

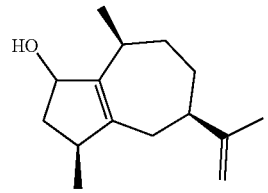

2

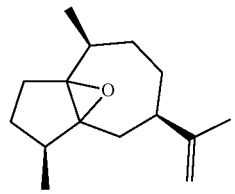

4

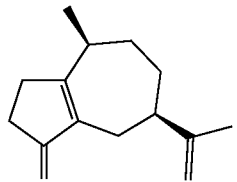

5

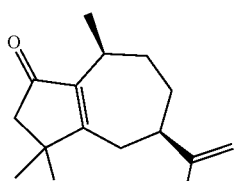

6

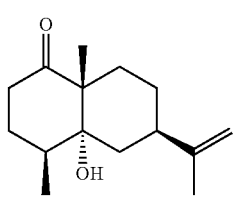

7

Components 1-7 as defined herein below are literature-known apart from ketone 5 which was isolated and its structure confirmed.

Nonpolar GC:
100° C./2 min, 15° C./min to 240° C., 240° C./5 min. Thermo Focus GC. Nonpolar column: Agilent Technologies J&W Scientific DB-5 (nonpolar, 5% phenylmethylpolysiloxane). Column dimensions: 30 m length, 0.32 mm ID, 0.25 μm film thickness. Injector: Split. Injector temperature: 240° C. Detector: FID. Detector temperature: 270° C. Injection volume: 1 μl. Carrier gas: Helium. Split ratio: 1/42.3. Pressure: 70 kPa. Integrator: Hewlett Packard.

By this method, substrate purity, conversion and GC-purities of rotundone 2 after distillation were determined (% rpa).

Source of α-Guaiene
α-Guaiene was isolated from Clearwood™ by repeated distillation with purities of 37% to 85%. The purities were determined by GC and NMR with internal standard anisaldehyde. The other constituents were seychellene (≤33%), α-patchoulene (≤25%), and γ-patchoulene (≤5%). The purity was determined by GC and NMR with internal standard anisaldehyde.

Clearwood™ (CAS 1450625-49-6) is a perfumery ingredient in the patchouli, woody family and commercially available from Firmenich. This mixture of sesquiterpenes, which contains about 14 wt.-% of α-guaiene 1, is obtained by fermentation of sugars (*IP.com Technical Disclosure IPCOM000233341D*).

Examples for the biotechnological production of α-guaiene 1 are also given in *Plant Physiol.* 2010, 154, 1998-2007; *Arch. Biochem. Biophys.* 2006, 454, 123-136 and WO 2005/052163 A2.

Preparation of Rotundone 2 from α-Guaiene 1 (Iron Porphyrin Catalysis)

Chloro(tetraphenylporphyrinato)iron(III) (17 mg, 0.024 mmol) and imidazole (6.7 mg, 0.1 mmol) were added to α-guaiene 1 (61% ex Clearwood™, 1 g, 3 mmol) in a 1:1 ethanol/water mixture (20 mL) under stirring. Oxygen was bubbled into the greenish turbid mixture at 45° C. After 30 min the oxygen inlet was replaced by an oxygen balloon. After 5 hours GC indicated complete conversion to a mixture containing of, rotundone 2 (24%), epoxy-guaiene 4 (3%), ketone 5 (6%), hydroxy-rotundone 6 (4%), seychellene 8 (37%). The dark-brown mixture was evaporated partially under reduced pressure and the residue extracted with tert-butyl methyl ether. The combined organic layers were dried over MgSO$_4$, filtered and evaporated. The residual brown oil (1.22 g) was bulb-to-bulb distilled at 150-230° C./0.03 mbar, giving 0.88 g rotundone 2 of 32% GC-purity (43% corr. yield) as a red-brown oil and 0.18 g of a brown residue.

Preparation of Rotundone 2 from α-Guaiene 1 (Organocatalysis)

In a 100 mL round-bottom two-necked flask equipped with a condenser, α-guaiene 1 (37% ex Clearwood™, 1.022 g, 1.85 mmol) and NHPI (0.082 g, 0.5 mmol) were dissolved in acetonitrile (30 mL) and water (15 mL) under positive nitrogen flow. The solution was heated to 50° C., and solid NaClO$_2$ (0.678 g, 7.5 mmol) was added in portions. The reaction mixture was then allowed to stir at 50° C. for 21 h. Then, the solution was allowed to cool to room temperature and poured onto NaOH (aqueous, 2M). The product was extracted with MTBE and washed with brine. The combined organic layers were dried over MgSO$_4$, filtered and evaporated. GCMS of the residue (0.92 g) indicated complete conversion to a mixture containing rotundone 2 (6%), rotundol 3 (1%), epoxy-guaiene 4 (1%), ketone 5 (1%), hydroxy-rotundone 6 (2%), seychellene (40%), α-patchoulene (11%), α-patchoulenone (2%) and β-patchoulenone (2%) The residual brown oil (0.92 g) was bulb-to-bulb distilled at 160-220° C./0.01 mbar, giving 0.92 g rotundone 2 of 17% GC-purity (33% corr. yield) as a red-brown oil and 90 mg of a brown residue.

Olfactory Description of Rotundone 2

(from iron porphyrin catalysis as described herein above, purified by distillation, dilution 1% in ethanol on blotter dipped freshly, after 4 h and after 1 week)

| Time | Olfactory Description |
|---|---|
| 2 minutes | fresh, woody, cedarwood, terpenic, wood fiber, slightly minty and terpinol |
| 4 hour | warm, woody, spicy, cedar wood like, wood fiber, sawdust, straw |
| 1 week | cedar wood like, wood fiber, sawdust, straw |

Synthesis and purification of Ketone 5

Oxygen was bubbled into a mixture of chloro(tetraphenylporphyrinato) iron(III) (34 mg, 0.05 mmol), imidazole (6.7 mg, 0.1 mmol) and α-guaiene 91% (1 g, 4.5 mmol) in polyethylenglycol (20 mL) under stirring, light irradiation with a 300 W Osram Ultra Vitalux lamp and at 45° C. After 38 hours, GCMS indicated a quantitative conversion to a mixture of rotundone 2 (27%), epoxy-guaiene 4 (6%), ketone 5 (11%), hydroxy-rotundone 6 (19%), corymbolon 7 (1%). The orange product mixture was extracted with tert-butyl methyl ether against water. The combined organic layers were dried over MgSO$_4$, filtered and evaporated to 0.7 g of an orange oil, which was purified by flash chromatography over 30 g silica gel 15-40 µm using an hexane/ethyl acetate gradient 98:2-50:50. After evaporation of the solvents this gave 0.23 g of rotundone 2 with 52-59% GC-purity (13% corr) and 24 mg of Ketone 5 with a GC-purity of 71% (2% corr). Ketone 5 was further purified by preparative GC to a purity of >99.5% (containing less than 0.03% of rotundone 2) and its odor analyzed on blotter and by sniff-GC being woody, cedary, dry, isoraldeine-guaiac, smokey, fruity, spicy.

Analytical data of ketone 5 ((4S,7R)-4-methyl-7-(prop-1-en-2-yl)-3,4,5,6,7,8-hexahydroazulen-1(2H)-one): $^1$H-NMR (benzene-D$_6$, 400 MHz): 4.85-4.9 (2 s, 2H), 3.1-3.14 (2 h), 2.5-1.4 (10H), 1.75 (s, 3H), 0.9 (d, 3H) ppm; $^{13}$C-NMR (benzene-D$_6$, 100 MHz): 206.5 (s), 176.6 (s), 150.3 (s), 139.0 (s), 108.9 (t), 45.2 (d), 36.4 (d), 33.8 (t), 32.1 (t), 30.9 (t), 29.5 (t), 28.1 (t), 20.4 (q), 16.5 (q) ppm; $^{13}$C-NMR (CDCl$_3$, 100 MHz): 209.3 (s), 179.9 (s), 150.6 (s), 139.2 (s), 108.9 (t), 45.3 (d), 36.85 (d), 34.3 (t), 32.3 (t), 31.0 (t), 30.15 (t), 27.2 (t), 20.6 (q), 17.0 (q) ppm; IR (cm$^{-1}$): 2661 (w), 2922 (m), 2854 (w), 1697 (s), 1642 (m), 1452 (w), 1438 (w), 1375 (w), 1304 (w), 1286 (w), 1260 (w), 1236 (w), 1173 (w), 1154 (w), 1071 (w), 1042 (w), 1023 (w), 992 (w), 886 (m), 532 (w); GCMS (EI, m/z): 204 (2%, [M]$^+$), 189 (11%, [M−15]$^+$), 161 (12%), 148 (51%), 147 (48%), 134 (10%), 133 (100%), 121 (18%), 119 (28%), 107 (19%), 106 (11%), 105 (43%), 93 (25%), 91 (18%), 91 (39%), 81 (34%), 81 (17%), 79 (27%), 77 (22%); $[α]_D^{22}$=−11.4 (c 0.35, CHCl$_3$); HRMS (ESI): Calculated for C$_{14}$H$_{21}$O [M+H]$^+$: 205.1587; Found: 205.1586.

The invention claimed is:

1. A process for producing rotundone from α-guaiene, wherein the α-guaiene is produced from a precursor by a sesquiterpene synthase, wherein the sesquiterpene synthase is produced in a microorganism, and wherein the sesquiterpene synthase has a sequence identity with SEQ ID NO.: 2, SEQ ID NO.: 4 or SEQ ID NO.: 6 of at least 70%.

2. The process according to claim 1, wherein the microorganism is cultured under conditions suitable to produce α-guaiene.

3. The process according to claim 1, wherein the sesquiterpene synthase is isolated from the microorganism prior to production of α-guaiene.

4. The process according to claim 1, wherein the microorganism is a recombinant microorganism.

5. The process according to claim 1, wherein the precursor is an acyclic precursor.

6. The process according to claim 1, wherein rotundone is produced from α-guaiene by an oxidation selected from the group consisting of transition metal catalysis, organocatalysis, chromium oxidation, selenium oxidation, manganese oxidation, aerial oxidation, enzymatic oxidation, electrochemical oxidation and combinations thereof.

7. The process according to claim 6, wherein rotundone is produced from α-guaiene by transition metal catalysis and the transition metal is selected from the group consisting of iron, copper, vanadium, manganese, molybdenum, cobalt, ruthenium, palladium, iridium, rhodium, titanium, chromium, gold, osmium and combinations thereof.

8. The process according to claim 7, wherein rotundone is produced from α-guaiene by iron porphyrin catalysis comprising the steps of:
Forming a mixture containing α-guaiene and an iron (III)-X porphyrin complex catalyst in a solvent;
Introducing molecular oxygen into the mixture;
Effecting production of rotundone oxidation of the C(3) position of α-guaiene.

9. The process according to claim 6, wherein rotundone is produced from α-guaiene by organocatalysis.

10. The process according to claim 1, wherein rotundone is produced from α-guaiene by oxidation of the C(3) position.

11. The process according to claim 5, wherein the precursor is farnesyl pyrophosphate.

12. The process according to claim 1, wherein the sesquiterpene synthase has a sequence identity with SEQ ID NO.: 2, SEQ ID NO.: 4 or SEQ ID NO.: 6 of at least 80%.

13. The process according to claim 12, wherein the sesquiterpene synthase has a sequence identity with SEQ ID NO.: 2, SEQ ID NO.: 4 or SEQ ID NO.: 6 of at least 90%.

14. The process according to claim 13, wherein the sesquiterpene synthase has a sequence identity with SEQ ID NO.: 2, SEQ ID NO.: 4 or SEQ ID NO.: 6 of at least 95%.

15. The process according to claim 9, wherein rotundone is produced from α-guaiene by organocatalysis comprising the steps of:

Forming a mixture containing α-guaiene, an organocatalyst, selected from the group consisting of N-hydroxyphthalimide and tetrachloro-N-hydroxyphthalimide, and an oxidant in a solvent; and Effecting oxidation of the C(3) position of α-guaiene.

* * * * *

SEQUENCE LISTING

<160> NUMBER OF SEQ ID NOS: 6

<210> SEQ ID NO 1
<211> LENGTH: 1686
<212> TYPE: DNA
<213> ORGANISM: Vitis vinifera

<400> SEQUENCE: 1

```
atgtctgttc cactatcagt ctcagtcact cctatactaa gccagaggat tgatcctgag    60
gtggctcgcc acgaagccac atatcatcct aacttctggg gtgatcgttt cctccactac   120
aatcctgatg atgatttctg tggaacccat gcttgtaaag aacaacaaat tcaagaactg   180
aaagaagaag tgcggaagag cctggaagct actgctggga cacttcaca gctgctgaag    240
ttgatagatt ccatccaacg cttgggattg gcttaccact ttgaaaggga gattgaagaa   300
gcattgaagg ccatgtatca aacttatact ctggttgatg ataatgatca cctcactaca   360
gtttcccttc tgttccgact actaagacag gaaggttacc acattccatc agatgtattt   420
aagaagttca tggatgaggg aggcaacttc aaggaatcat tggtgggtga cttaccaggc   480
atgctagctt tatatgaagc tgcacattta atggtgcatg gagaagacat actagatgaa   540
gccctgggtt tcaccactgc tcaccttcag tccatggcaa ttgattcaga taatcctctc   600
acaaaacaag tgattcgtgc tctaaagcgc ccgattcgca agggcttacc aagggtggag   660
gcaaggcatt acattaccat ctaccaagaa gacgattcac ataatgaatc tttactcaag   720
cttgcaaagt tggattacaa catgttgcag tcactccaca ggaaagagct aagtgagatc   780
actaagtggt ggaaaggttt agactttgcg acaaagctac ttttgcgag ggacaggata    840
gtggaaggct acttttggat cttgggagtg tactttgaac cccaatatta ccttgctaga   900
aggatcttaa tgaaagtatt cggggtgcta tccattgtag atgatatata tgatgcgtat   960
gggacatttg aagaactcaa actctttaca gaagcaattg agagatggga tgccagcagc  1020
atagatcaac tgccagatta tatgaaggtg tgttatcagg ctctcttaga tgtctatgaa  1080
gaaatggagg aagagatgac gaagcaagga aaactgtacc gtgttcacta cgcacaagca  1140
gcgttaaaaa ggcaagtcca agcctacctt cttgaagcca atggttgaa  gcaagaatat  1200
ataccaacaa tggaagagta catgagcaac gcgctggtaa cgtctgcctg ctctatgctt  1260
acaaccacat ctttcgtcgg tatgggagat atggtaacca aggaggcctt cgattgggtt  1320
ttcagtgacc ctaagatgat tagagcttca aacgtcattt gcaggcttat ggatgacata  1380
gtttcccatg agtttgagca aaaaagaggg catgttgcct cagccgtaga atgctacatg  1440
gtgcaatatg gggtttcaaa ggaagaagct tatgatgagt tcaagaagca agtagagagt  1500
gcatggaagg ataataatga ggagttcctg caacctacag cagtgccagt tccactcctc  1560
acccgtgttc tgaattttag ccggatggtg gacgtcttgt acaaggacga agatgagtac  1620
acgctggttg gaccattgat gaaagatctg gttgcaggga tgctcataga tcctgtgcca  1680
atgtaa                                                              1686
```

<210> SEQ ID NO 2
<211> LENGTH: 561
<212> TYPE: PRT
<213> ORGANISM: Vitis vinifera

<400> SEQUENCE: 2

```
Met Ser Val Pro Leu Ser Val Ser Val Thr Pro Ile Leu Ser Gln Arg
1               5                   10                  15

Ile Asp Pro Glu Val Ala Arg His Glu Ala Thr Tyr His Pro Asn Phe
            20                  25                  30

Trp Gly Asp Arg Phe Leu His Tyr Asn Pro Asp Asp Phe Cys Gly
        35                  40                  45

Thr His Ala Cys Lys Glu Gln Gln Ile Gln Glu Leu Lys Glu Glu Val
    50                  55                  60
```

```
Arg Lys Ser Leu Glu Ala Thr Ala Gly Asn Thr Ser Gln Leu Leu Lys
 65                  70                  75                  80

Leu Ile Asp Ser Ile Gln Arg Leu Gly Leu Ala Tyr His Phe Glu Arg
                 85                  90                  95

Glu Ile Glu Glu Ala Leu Lys Ala Met Tyr Gln Thr Tyr Thr Leu Val
            100                 105                 110

Asp Asp Asn Asp His Leu Thr Thr Val Ser Leu Leu Phe Arg Leu Leu
            115                 120                 125

Arg Gln Glu Gly Tyr His Ile Pro Ser Asp Val Phe Lys Lys Phe Met
            130                 135                 140

Asp Glu Gly Gly Asn Phe Lys Glu Ser Leu Val Gly Asp Leu Pro Gly
145                 150                 155                 160

Met Leu Ala Leu Tyr Glu Ala Ala His Leu Met Val His Gly Glu Asp
                165                 170                 175

Ile Leu Asp Glu Ala Leu Gly Phe Thr Thr Ala His Leu Gln Ser Met
            180                 185                 190

Ala Ile Asp Ser Asp Asn Pro Leu Thr Lys Gln Val Ile Arg Ala Leu
            195                 200                 205

Lys Arg Pro Ile Arg Lys Gly Leu Pro Arg Val Glu Ala Arg His Tyr
210                 215                 220

Ile Thr Ile Tyr Gln Glu Asp Asp Ser His Asn Glu Ser Leu Leu Lys
225                 230                 235                 240

Leu Ala Lys Leu Asp Tyr Asn Met Leu Gln Ser Leu His Arg Lys Glu
                245                 250                 255

Leu Ser Glu Ile Thr Lys Trp Trp Lys Gly Leu Asp Phe Ala Thr Lys
            260                 265                 270

Leu Pro Phe Ala Arg Asp Arg Ile Val Glu Gly Tyr Phe Trp Ile Leu
            275                 280                 285

Gly Val Tyr Phe Glu Pro Gln Tyr Tyr Leu Ala Arg Arg Ile Leu Met
290                 295                 300

Lys Val Phe Gly Val Leu Ser Ile Val Asp Asp Ile Tyr Asp Ala Tyr
305                 310                 315                 320

Gly Thr Phe Glu Glu Leu Lys Leu Phe Thr Glu Ala Ile Glu Arg Trp
                325                 330                 335

Asp Ala Ser Ser Ile Asp Gln Leu Pro Asp Tyr Met Lys Val Cys Tyr
            340                 345                 350

Gln Ala Leu Leu Asp Val Tyr Glu Glu Met Glu Glu Met Thr Lys
            355                 360                 365

Gln Gly Lys Leu Tyr Arg Val His Tyr Ala Gln Ala Ala Leu Lys Arg
            370                 375                 380

Gln Val Gln Ala Tyr Leu Leu Glu Ala Lys Trp Leu Lys Gln Glu Tyr
385                 390                 395                 400

Ile Pro Thr Met Glu Glu Tyr Met Ser Asn Ala Leu Val Thr Ser Ala
                405                 410                 415

Cys Ser Met Leu Thr Thr Thr Ser Phe Val Gly Met Gly Asp Met Val
            420                 425                 430

Thr Lys Glu Ala Phe Asp Trp Val Phe Ser Asp Pro Lys Met Ile Arg
            435                 440                 445

Ala Ser Asn Val Ile Cys Arg Leu Met Asp Asp Ile Val Ser His Glu
            450                 455                 460

Phe Glu Gln Lys Arg Gly His Val Ala Ser Ala Val Glu Cys Tyr Met
465                 470                 475                 480
```

```
Lys Gln Tyr Gly Val Ser Lys Glu Glu Ala Tyr Asp Glu Phe Lys Val
                485                 490                 495

Gln Val Glu Ser Ala Trp Lys Asp Asn Asn Glu Glu Phe Leu Gln Pro
            500                 505                 510

Thr Ala Val Pro Val Pro Leu Leu Thr Arg Val Leu Asn Phe Ser Arg
        515                 520                 525

Met Val Asp Val Leu Tyr Lys Asp Glu Asp Glu Tyr Thr Leu Val Gly
    530                 535                 540

Pro Leu Met Lys Asp Leu Val Ala Gly Met Leu Ile Asp Pro Val Pro
545                 550                 555                 560

Met

<210> SEQ ID NO 3
<211> LENGTH: 1644
<212> TYPE: DNA
<213> ORGANISM: Aquilaria

<400> SEQUENCE: 3
atgtcttcgg caaaactagg ttctgcctcc gaagatgtta gccgccgaga tgccaattac        60
catcccaccg tttgggggga cttttcctc actcattctt ccaacttctt ggaaaataac       120
gacagcatcc ttgaaaaaca tgaggagttg aaacaagaag tgagaaactt gttggtagtt       180
gaaacaagtg atcttccaag caagatccaa ttgactgacg aaatcattcg tctgggcgtt       240
ggatatcatt ttgagacgga gatcaaagct caactggaga aattgcatga tcaccaactt       300
catctcaatt tcgatctcct cacgacatcc gtttggtttc ggttgcttcg aggacacgga       360
ttctctattc catccgatgt gttcaaaaga ttcaagaaca caaagggtga attcgagact       420
gaggatgcga ggactttgtg tgtttgtat gaagcaacac atctaagagt tgatggtgaa       480
gatatattgg aagaagccat tcaattttca aggaaaagat tggaggctct cttgccgaaa       540
ttaagcttcc ctctcagcga atgcgtgagg gacgctcttc acattcctta ccaccggaat       600
gttcaaaggt tggctgcaag gcaatacatt ccccaatatg acgcagaaca aacaaagatc       660
gagtcattgt ccttgtttgc caaaatcgac tttaacatgt tgcaagcttt acaccaaagt       720
gaactaagag aagcttctcg ttggtggaag gaatttgatt ttccatccaa gcttccttat       780
gcaagagaca gaattgctga aggctactac tggatgatgg gtgcccattt tgagcctaaa       840
ttctctctta gtagaaaatt tctcaataga atagttggga ttacttctct aatcgatgac       900
acatatgatg tttatggcac attggaagaa gttacgttgt tcactgaagc agtcgagagg       960
tgggacattg aagctgtaaa agatattcct aaatacatgc aagtaattta cattggtatg      1020
ttgggcattt ttgaagattt caaggacaat ctgatcaatg caagagggaa agactattgc      1080
attgattatg cgatagaagt gtttaaggag attgtcagat cttaccaaag agaagcagag      1140
tatttccaca ctggatatgt gcctagttat gacgagtaca tggagaactc cataataagt      1200
ggtgggtaca gatgttcat tattctgatg ttgattggaa gggagagtt tgaactcaag      1260 gaaactctag attgggcttc gacaatccca gaaatggtca agcttcttc gcttatcgct      1320 cgttatattg tgaccttca gacctacaag gccgaagagg aaagagggga aaccgtttcg      1380
gcggtgcggt gttacatgag ggagtttggc gtttcagaag aacaggcatg caagaagatg      1440
agggagatga ttgagatcga gtggaaaaga ctgaacaaga cgaccctaga ggcggatgaa      1500
atctcttcgt cggttgtgat cccatcccta aatttcactc gagtgttgga ggtgatgtac      1560
gataaaggtg atggatacag cgattctcaa ggcgtgacca aggatagaat tgctgccttg      1620
```

```
ttgcgtcatg ctattgaaat ctga                                              1644
```

<210> SEQ ID NO 4
<211> LENGTH: 547
<212> TYPE: PRT
<213> ORGANISM: Aquilaria

<400> SEQUENCE: 4

```
Met Ser Ser Ala Lys Leu Gly Ser Ala Ser Glu Asp Val Ser Arg Arg
1               5                   10                  15

Asp Ala Asn Tyr His Pro Thr Val Trp Gly Asp Phe Phe Leu Thr His
                20                  25                  30

Ser Ser Asn Phe Leu Glu Asn Asn Asp Ser Ile Leu Glu Lys His Glu
            35                  40                  45

Glu Leu Lys Gln Glu Val Arg Asn Leu Leu Val Val Glu Thr Ser Asp
        50                  55                  60

Leu Pro Ser Lys Ile Gln Leu Thr Asp Glu Ile Ile Arg Leu Gly Val
65                  70                  75                  80

Gly Tyr His Phe Glu Thr Glu Ile Lys Ala Gln Leu Glu Lys Leu His
                85                  90                  95

Asp His Gln Leu His Leu Asn Phe Asp Leu Leu Thr Thr Ser Val Trp
            100                 105                 110

Phe Arg Leu Leu Arg Gly His Gly Phe Ser Ile Pro Ser Asp Val Phe
        115                 120                 125

Lys Arg Phe Lys Asn Thr Lys Gly Glu Phe Glu Thr Glu Asp Ala Arg
    130                 135                 140

Thr Leu Trp Cys Leu Tyr Glu Ala Thr His Leu Arg Val Asp Gly Glu
145                 150                 155                 160

Asp Ile Leu Glu Glu Ala Ile Gln Phe Ser Arg Lys Arg Leu Glu Ala
                165                 170                 175

Leu Leu Pro Lys Leu Ser Phe Pro Leu Ser Glu Cys Val Arg Asp Ala
            180                 185                 190

Leu His Ile Pro Tyr His Arg Asn Val Gln Arg Leu Ala Ala Arg Gln
        195                 200                 205

Tyr Ile Pro Gln Tyr Asp Ala Glu Gln Thr Lys Ile Glu Ser Leu Ser
    210                 215                 220

Leu Phe Ala Lys Ile Asp Phe Asn Met Leu Gln Ala Leu His Gln Ser
225                 230                 235                 240

Glu Leu Arg Glu Ala Ser Arg Trp Trp Lys Glu Phe Asp Phe Pro Ser
                245                 250                 255

Lys Leu Pro Tyr Ala Arg Asp Arg Ile Ala Glu Gly Tyr Tyr Trp Met
            260                 265                 270

Met Gly Ala His Phe Glu Pro Lys Phe Ser Leu Ser Arg Lys Phe Leu
        275                 280                 285

Asn Arg Ile Val Gly Ile Thr Ser Leu Ile Asp Asp Thr Tyr Asp Val
    290                 295                 300

Tyr Gly Thr Leu Glu Glu Val Thr Leu Phe Thr Glu Ala Val Glu Arg
305                 310                 315                 320

Trp Asp Ile Glu Ala Val Lys Asp Ile Pro Lys Tyr Met Gln Val Ile
                325                 330                 335

Tyr Ile Gly Met Leu Gly Ile Phe Glu Asp Phe Lys Asp Asn Leu Ile
            340                 345                 350

Asn Ala Arg Gly Lys Asp Tyr Cys Ile Asp Tyr Ala Ile Glu Val Phe
        355                 360                 365
```

```
Lys Glu Ile Val Arg Ser Tyr Gln Arg Glu Ala Glu Tyr Phe His Thr
370                 375                 380
Gly Tyr Val Pro Ser Tyr Asp Glu Tyr Met Glu Asn Ser Ile Ile Ser
385                 390                 395                 400
Gly Gly Tyr Lys Met Phe Ile Ile Leu Met Leu Ile Gly Arg Gly Glu
                405                 410                 415
Phe Glu Leu Lys Glu Thr Leu Asp Trp Ala Ser Thr Ile Pro Glu Met
                420                 425                 430
Val Lys Ala Ser Ser Leu Ile Ala Arg Tyr Ile Asp Asp Leu Gln Thr
                435                 440                 445
Tyr Lys Ala Glu Glu Glu Arg Gly Glu Thr Val Ser Ala Val Arg Cys
450                 455                 460
Tyr Met Arg Glu Phe Gly Val Ser Glu Glu Gln Ala Cys Lys Lys Met
465                 470                 475                 480
Arg Glu Met Ile Glu Ile Glu Trp Lys Arg Leu Asn Lys Thr Thr Leu
                485                 490                 495
Glu Ala Asp Glu Ile Ser Ser Ser Val Val Ile Pro Ser Leu Asn Phe
                500                 505                 510
Thr Arg Val Leu Glu Val Met Tyr Asp Lys Gly Asp Gly Tyr Ser Asp
                515                 520                 525
Ser Gln Gly Val Thr Lys Asp Arg Ile Ala Ala Leu Leu Arg His Ala
                530                 535                 540
Ile Glu Ile
545

<210> SEQ ID NO 5
<211> LENGTH: 1659
<212> TYPE: DNA
<213> ORGANISM: Pogostemon cablin

<400> SEQUENCE: 5
atggagttgt atgcccaaag tgttggagtg ggtgctgctt ctcgtcctct tgcgaatttt      60
catccatgtg tgtggggaga caaattcatt gtctacaacc acaatcatg ccaggctgga     120
gagagagaag aggctgagga gctgaaagtg agctgaaaaa gagagctgaa ggaagcatca     180
gacaactaca tgcggcaact gaaaatggtg gatgcaatac aacgattagg cattgactat     240
cttttgtgg aagatgttga tgaagctttg aagaatctgt ttgaaatgtt tgatgctttc     300
tgcaagaata atcatgacat gcacgccact gctctcagct ttcgccttct cagacaacat     360
ggatacagag tttcatgtga agttttgaa aagtttaagg atggcaaaga tggatttaag     420
gttccaaatg aggatggagc ggttgcagtc cttgaattct tcgaagccac gcatctcaga     480
gtccatggag aagacgtcct tgataatgct tttgacttca ctaggaacta cttggaatca     540
gtctatgcaa ctttgaacga tccaaccgcg aaacaagtcc acaacgcatt gaatgagttc     600
tcttttcgaa gaggattgcc acgcgtggaa gcaggaagt acatatcaat ctacgagcaa     660
tacgcatctc atcacaaagg cttgctcaaa cttgctaagc tggatttcaa cttggtacaa     720
gctttgcaca gaagggagct gagtgaagat tctaggtggt ggaagacttt acaagtgccc     780
acaaagctat cattcgttag agatcgattg gtggagtcct acttctgggc ttcgggatct     840
tatttcgaac cgaattattc ggtagctagg atgatttag caaaagggct ggctgtatta     900
tctcttatgg atgatgtgta tgatgcatat ggtacttttg aggaattaca aatgttcaca     960
gatgcaatcg aaaggtggga tgcttcatgt ttagataaac ttccagatta catgaaaata    1020
gtatacaagg ccccttttga tgtgtttgag gaagttgacg aggagttgat caagctaggc    1080
```

```
gcaccatatc gagcctacta tggaaaagaa gccatgaaat acgccgcgag agcttacatg   1140
gaagaggccc aatggaggga gcaaaagcac aaacccacaa ccaaggagta tatgaagctg   1200
gcaaccaaga catgtggcta cataactcta ataatattat catgtcttgg agtggaagag   1260
ggcattgtga ccaaagaagc cttcgattgg gtgttctccc gacctccttt catcgaggct   1320
acattaatca ttgccaggct cgtcaatgat attacaggac acgagtttga gaaaaaacga   1380
gagcacgttc gcactgcagt agaatgctac atggaagagc acaaagtggg gaagcaagag   1440
gtggtgtctg aattctacaa ccaaatggag tcagcatgga aggacattaa tgagggttc    1500 ctcagaccag ttgaatttcc aatccctcta ctttatctta ttctcaattc agtccgaaca   1560
cttgaggtta tttacaaaga gggcgattcg tatacacacg tgggtcctgc aatgcaaaac   1620
atcatcaagc agttgtacct tcaccctgtt ccatattaa                          1659
```

<210> SEQ ID NO 6
<211> LENGTH: 552
<212> TYPE: PRT
<213> ORGANISM: Pogostemon cablin

<400> SEQUENCE: 6

```
Met Glu Leu Tyr Ala Gln Ser Val Gly Val Gly Ala Ala Ser Arg Pro
1               5                   10                  15

Leu Ala Asn Phe His Pro Cys Val Trp Gly Asp Lys Phe Ile Val Tyr
            20                  25                  30

Asn Pro Gln Ser Cys Gln Ala Gly Glu Arg Glu Glu Ala Glu Glu Leu
        35                  40                  45

Lys Val Glu Leu Lys Arg Glu Leu Lys Glu Ala Ser Asp Asn Tyr Met
    50                  55                  60

Arg Gln Leu Lys Met Val Asp Ala Ile Gln Arg Leu Gly Ile Asp Tyr
65                  70                  75                  80

Leu Phe Val Glu Asp Val Asp Glu Ala Leu Lys Asn Leu Phe Glu Met
                85                  90                  95

Phe Asp Ala Phe Cys Lys Asn Asn His Asp Met His Ala Thr Ala Leu
            100                 105                 110

Ser Phe Arg Leu Leu Arg Gln His Gly Tyr Arg Val Ser Cys Glu Val
        115                 120                 125

Phe Glu Lys Phe Lys Asp Gly Lys Asp Gly Phe Lys Val Pro Asn Glu
    130                 135                 140

Asp Gly Ala Val Ala Val Leu Glu Phe Phe Glu Ala Thr His Leu Arg
145                 150                 155                 160

Val His Gly Glu Asp Val Leu Asp Asn Ala Phe Asp Phe Thr Arg Asn
                165                 170                 175

Tyr Leu Glu Ser Val Tyr Ala Thr Leu Asn Asp Pro Thr Ala Lys Gln
            180                 185                 190

Val His Asn Ala Leu Asn Glu Phe Ser Phe Arg Arg Gly Leu Pro Arg
        195                 200                 205

Val Glu Ala Arg Lys Tyr Ile Ser Ile Tyr Glu Gln Tyr Ala Ser His
    210                 215                 220

His Lys Gly Leu Leu Lys Leu Ala Lys Leu Asp Phe Asn Leu Val Gln
225                 230                 235                 240

Ala Leu His Arg Arg Glu Leu Ser Glu Asp Ser Arg Trp Trp Lys Thr
                245                 250                 255

Leu Gln Val Pro Thr Lys Leu Ser Phe Val Arg Asp Arg Leu Val Glu
            260                 265                 270
```

-continued

```
Ser Tyr Phe Trp Ala Ser Gly Ser Tyr Phe Glu Pro Asn Tyr Ser Val
        275                 280                 285

Ala Arg Met Ile Leu Ala Lys Gly Leu Ala Val Leu Ser Leu Met Asp
    290                 295                 300

Asp Val Tyr Asp Ala Tyr Gly Thr Phe Glu Glu Leu Gln Met Phe Thr
305                 310                 315                 320

Asp Ala Ile Glu Arg Trp Asp Ala Ser Cys Leu Asp Lys Leu Pro Asp
                325                 330                 335

Tyr Met Lys Ile Val Tyr Lys Ala Leu Leu Asp Val Phe Glu Glu Val
            340                 345                 350

Asp Glu Glu Leu Ile Lys Leu Gly Ala Pro Tyr Arg Ala Tyr Tyr Gly
        355                 360                 365

Lys Glu Ala Met Lys Tyr Ala Ala Arg Ala Tyr Met Glu Glu Ala Gln
    370                 375                 380

Trp Arg Glu Gln Lys His Lys Pro Thr Thr Lys Glu Tyr Met Lys Leu
385                 390                 395                 400

Ala Thr Lys Thr Cys Gly Tyr Ile Thr Leu Ile Ile Leu Ser Cys Leu
                405                 410                 415

Gly Val Glu Glu Gly Ile Val Thr Lys Glu Ala Phe Asp Trp Val Phe
            420                 425                 430

Ser Arg Pro Pro Phe Ile Glu Ala Thr Leu Ile Ile Ala Arg Leu Val
        435                 440                 445

Asn Asp Ile Thr Gly His Glu Phe Glu Lys Lys Arg Glu His Val Arg
    450                 455                 460

Thr Ala Val Glu Cys Tyr Met Glu Glu His Lys Val Gly Lys Gln Glu
465                 470                 475                 480

Val Val Ser Glu Phe Tyr Asn Gln Met Glu Ser Ala Trp Lys Asp Ile
                485                 490                 495

Asn Glu Gly Phe Leu Arg Pro Val Glu Phe Pro Ile Pro Leu Leu Tyr
            500                 505                 510

Leu Ile Leu Asn Ser Val Arg Thr Leu Glu Val Ile Tyr Lys Glu Gly
        515                 520                 525

Asp Ser Tyr Thr His Val Gly Pro Ala Met Gln Asn Ile Ile Lys Gln
    530                 535                 540

Leu Tyr Leu His Pro Val Pro Tyr
545                 550
```